United States Patent
Traversaz et al.

(10) Patent No.: US 9,770,550 B2
(45) Date of Patent: Sep. 26, 2017

(54) ANTI-BOLUS CONTROL METHOD AND CORRESPONDING DEVICE

(75) Inventors: Philippe Traversaz, Saint-Blaise du Buis (FR); Damien Archat, Grenoble (FR)

(73) Assignee: FRESENIUS VIAL SAS, Brézins (FR)

( * ) Notice: Subject to any disclaimer, the term of this patent is extended or adjusted under 35 U.S.C. 154(b) by 143 days.

(21) Appl. No.: 13/499,734

(22) PCT Filed: Sep. 29, 2010

(86) PCT No.: PCT/EP2010/064450
§ 371 (c)(1),
(2), (4) Date: May 7, 2012

(87) PCT Pub. No.: WO2011/039250
PCT Pub. Date: Apr. 7, 2011

(65) Prior Publication Data
US 2012/0215170 A1     Aug. 23, 2012

(30) Foreign Application Priority Data
Oct. 2, 2009   (FR) ..................... 09 56874

(51) Int. Cl.
*A61M 5/145* (2006.01)
(52) U.S. Cl.
CPC ....... *A61M 5/14546* (2013.01); *A61M 5/1456* (2013.01)
(58) Field of Classification Search
CPC ............ A61M 5/14546; A61M 5/1456; A61M 1/0068; A61M 5/1452; A61M 5/1468; A61M 2005/14573
(Continued)

(56) References Cited

U.S. PATENT DOCUMENTS 4,424,720 A * 1/1984 Bucchianeri ............... 74/424.78
4,544,369 A * 10/1985 Skakoon et al. ............ 604/155
(Continued)

FOREIGN PATENT DOCUMENTS

DE   42 13 172 C1   5/1993
EP   0 314 880 A2   5/1989
(Continued)

OTHER PUBLICATIONS

Machine translation of DE 4213172/EP 0566825. Retrieved on Jul. 25, 2015.*
(Continued)

*Primary Examiner* — Nathan R Price
*Assistant Examiner* — Weng Lee
(74) *Attorney, Agent, or Firm* — Westerman, Hattori, Daniels & Adrian, LLP (57) ABSTRACT

For controlling the movement of the push device of a pump of the syringe driver-type, the pump comprising a casing (100), a syringe cradle (200) for a syringe (400), a push device (300) mobile relative to the casing (100) and capable of being driven in rotation parallel to the longitudinal axis of the syringe by driving means, clutch means (310, 350, 351) for engaging or disengaging the push device on the driving means, the push device is disengaged from the driving means, in order to move it manually, and the presence or absence of a contact between the push device and the syringe head is determined. If the push device is not in contact with the syringe head, it is advanced manually. Blocking of the advance movement of the push device is triggered only if, at the beginning, the push device was not in contact with the syringe head.

30 Claims, 9 Drawing Sheets

(58) Field of Classification Search
USPC .................. 128/DIG. 1, DIG. 12, DIG. 13; 604/65–67, 131
See application file for complete search history.

(56) References Cited

U.S. PATENT DOCUMENTS

| | | | |
|---|---|---|---|
| 4,988,337 A | | 1/1991 | Ito |
| 5,006,112 A | | 4/1991 | Metzner |
| 5,545,140 A | * | 8/1996 | Conero et al. ............... 604/154 |
| 5,879,360 A | | 3/1999 | Crankshaw |
| 6,575,936 B1 | * | 6/2003 | Kojima et al. ............... 604/155 |
| 6,932,242 B2 | | 8/2005 | Gerlach et al. |
| 6,958,053 B1 | * | 10/2005 | Reilly ........................... 604/154 |
| 7,422,570 B2 | * | 9/2008 | Gerlach et al. ............... 604/154 |
| 7,543,516 B2 | * | 6/2009 | Siefert ................ A61M 5/1456 74/424.78 |
| 2004/0064041 A1 | * | 4/2004 | Lazzaro et al. ............... 600/432 |
| 2009/0157003 A1 | * | 6/2009 | Jones et al. ................... 604/131 |

FOREIGN PATENT DOCUMENTS

| | | |
|---|---|---|
| EP | 0 354 852 A2 | 2/1990 |
| EP | 0566825 A1 | 10/1993 |
| EP | 1 329 232 A1 | 7/2003 |
| EP | 1 374 932 A2 | 1/2004 |
| JP | H2-211174 A | 8/1990 |
| JP | 2002-191693 A | 7/2002 |
| JP | 2003-235969 A | 8/2003 |
| JP | 2007-306991 A | 11/2007 |

OTHER PUBLICATIONS

Machine translation of EP 0314880 A2. Retrieved on Jul. 25, 2015.*
International Preliminary Report on Patentability of International Application No. PCT/EP2010/064450 (Form PCT/IBEA/409) dated Apr. 2, 2012, w/ English translation (20 pages).
International Search Report of PCT/EP2010/064450, mailing date of Feb. 1, 2011.
Japanese Office Action dated Jul. 9, 2014 in co-pending Japanese application No. 2012-531407; with English machine translation (6 pages).
Japanese Office Action dated Dec. 16, 2014 in co-pending Japanese application No. 2012-531407; with English machine translation (4 pages).

* cited by examiner

ANTI-BOLUS CONTROL METHOD AND CORRESPONDING DEVICE

The invention concerns a method of controlling the movement of a push device of a pump of the syringe driver-type, the pump comprising a casing, a syringe cradle in which a syringe is placed, a push device mobile relative to the casing and capable of being driven in translation parallel to the longitudinal axis of the syringe by driving means, and clutch means for engaging or disengaging the push device on the driving means. The invention also concerns a pump of the syringe driver-type for implementing the method.

Syringe drivers are frequently used in medicine to administer a solution at a relatively slow speed, for example, for pain therapy or in anesthesia. They are usually made up of a casing equipped with a cradle intended to receive a syringe containing the liquid for the perfusion and a push device that pushes the head of the syringe at a speed defined so as to cause the liquid contained in the syringe to flow out. The movement of the push device is brought about by driving means ordinarily constituted by a threaded driving rod driven in rotation by a motor. A nut integral with the push device is linked to the threaded driving rod, so that the rotation of the latter triggers the translation of the nut, and thus, of the push device. This nut is usually constituted by two half-nuts whose function will be explained below.

When such a syringe is put in place, it is necessary, first of all, to move the push device away, to put the syringe in place in the syringe cradle and to block it, in particular in the axial direction, by adapted means, and then to bring the push device back in contact with the syringe head. This head is constituted by a radial plate located at the free end of the syringe piston. The fast movement of the push device in direction of the syringe head can be performed manually or automatically. For the manual movement of the push device, it is necessary, first of all, to disengage the driving means. To this effect, the two half-nuts are moved away from each other and thus separated from the threaded driving rod. In this disengaged position, they are no longer linked to the threaded driving rod, and it is possible to manually move the push device.

During this last operation, it occurs that an involuntary bolus (fast administration of a dose) is delivered at the instant when the push device comes to hit against the syringe. Such a bolus can have dramatic consequences.

Documents EP 1 329 232 A1 and EP 1 374 932 A2 describe a braking device that is intended to prevent the piston from advancing when the push device comes in contact with the syringe head. The syringe is put in place in the traditional way in the syringe cradle, then, a braking device, in the form of a blade, comes to bear radially against the fins of the piston and blocks the latter in translation. When the push device is advanced, it can hit the syringe head without triggering a movement of the piston. Once the push device has been contacted with the syringe head, the braking device is moved away and the motor of the syringe push device is actuated. The drawback of such a braking device is that it can damage the piston or get the piston stuck in the cylinder of the syringe. In addition, in order to operate properly, the blades must be sharpened sufficiently to dig into the piston of the syringe, otherwise the piston would not be sufficiently maintained. However, if the blades are sufficiently sharpened, they also represent a danger for the operator who could get hurt by these blades, in particular, when there is a malfunction.

The objective of the invention is thus to develop a new method and a new pump that can prevent the involuntary administration of a bolus, but without the risk of damaging the syringe or injuring the pump users. Another objective of the invention is to make it possible to administrate a voluntary bolus.

This objective is reached by the method of the invention. First of all, the push device is disconnected from the driving means, which makes it possible to move it manually, and the presence or absence of a contact between the push device and the syringe head is determined. If the push device is not in contact with the syringe head, it is advanced manually toward the latter. As soon as the push device comes in contact with the syringe head, the advance movement of the push device is stopped by actuating means for blocking the movement of the push device which had been deactivated up to then. During this entire step, even when the push device has come in contact with the syringe head, the latter can be moved in the direction of the syringe by other means than the push device, for example, with using a finger. Blocking of the advance movement of the push device is triggered only if, at the beginning of the operation, the push device was not in contact with the syringe head. Contrary to the state of the art, it is not the syringe piston that is blocked, but the movement of the push device that is stopped as soon as there is contact between the syringe and the push device. As long as this contact does not exist, no element is blocked and no blocking means is activated.

Once the push device has come in contact with the syringe head and its advance movement has been blocked, it is again possible to engage the push device on the driving means. This clutch ensures a coupling of the push device on the driving motor. The push device can no longer move as long as the motor is not actuated. It is thus possible to unblock the push device.

Occasionally, it is required to administer a voluntary bolus. It is thus necessary to allow the movement of the piston even when the latter is in contact with the syringe head. To this effect, the method provides for disengaging again the push device from the driving means, then moving in translation, by the desired amplitude, the push device in contact with the syringe head toward the syringe, and finally stopping the movement of the push device and engaging again the push device on the driving means. These steps can be performed only if, at the beginning of the voluntary bolus procedure, the push device is already in contact with the syringe head. It is thus possible to administer this voluntary bolus directly after the push device has been contacted with the syringe head and its movement has been unblocked, or else, during a perfusion.

After the step of contacting the push device with the syringe head followed by unblocking the push device movement, or after the voluntary bolus step, the driving means can be started.

When the method is applied to a pump whose push device is driven by a threaded driving rod by means of two half-nuts that can be moved between an engaged position in which the two half-nuts are brought close to each other and surrounding the threaded driving rod so that they can move on the latter only if it is set in rotation, and a disengaged position in which the two half-nuts are moved away from each other and disconnected from the threaded driving rod so that they no longer cooperate with it, it can occur that, at the end of the manual movement to bring the push device close to the syringe head or to administer a voluntary bolus, the two half-nuts are not aligned with the thread of the threaded diving rod, in other words, they do not fall in the recesses of the thread of the driving screw. It is thus appropriate to perform a specific sequence in order to correct this shift. To this effect, after the engagement that follows the manual displacement of the push device, either to bring it closer to the syringe head or to administer a voluntary bolus, the relative position of the half-nuts is detected, and, as the case may be, if they have not reached the engaged position, the threaded driving rod is set in rotation while containing the effort generated by the push device, using a force sensor, for example, as long as the engaged position has not been reached.

The invention also concerns a pump of the syringe driver-type for implementing the method. This pump comprises a casing, a syringe cradle intended to receive a syringe, a push device mobile relative to the casing and capable of being driven in translation parallel to a longitudinal axis of the syringe by driving means, clutch means for engaging or disengaging the push device on driving means, the pump being equipped with means for blocking the movement of the push device toward the syringe when the push device comes in contact with the syringe head during a movement from a position without contact with the syringe head toward a position in contact with the syringe head. The pump of the invention is characterized by the fact that the means for blocking the push device comprise a threaded control rod, a nut engaged on the threaded rod and integral with the push device, a brake capable of acting on the threaded control rod. Thus, as soon as the contact between the push device and the syringe head is detected, the brake blocks the rotation of the threaded control rod. The nut, which is itself blocked in rotation by being integral with the push device, can thus no longer move on the threaded control rod. The same applies to the push device which is integral with this nut. Blocking of the push device is thus performed without any intervention on the syringe itself As a result, the device does not run the risk of getting the syringe piston damaged or stuck.

In an embodiment of the invention, the brake is constituted by an electromagnetic brake comprising a rotor integral with the threaded control rod and a stator integral with the casing.

It is in conformity with the invention to equip the push device with a sensor to detect the presence or the absence of contact between the push device and the syringe head. If this sensor is an electrical sensor, its signal can be used directly to transmit a blocking signal to the electromagnetic brake.

It is preferable if the driving means is constituted by a motor and a threaded driving rod driven in rotation by the motor. Then, the clutch means can be constituted by a lever located outside the casing, a push rod fixed to the lever and two half-nuts that can be moved from an engaged position in which they surround the threaded driving rod so that they can cooperate with it and an unengaged position in which they are moved away from the threaded driving gear so that they do not cooperate with it.

It is preferable to provide at least one engagement sensor to determine if the push device is engaged or disengaged on the clutch means. These engagement sensors can be placed on the push device and/or on the clutch means.

An example of embodiment is presented below in reference to the drawings, which show.

The method and device of the invention are intended for a pump of the syringe driver-type. Like any syringe driver, it comprises, in particular a casing (100), on the front face of which is located a syringe cradle (200) intended to receive a syringe, a push device (300) intended to push the head (401) of the syringe (400) to cause the piston (402) of the syringe to penetrate into the cylinder (403) and thus expel the content of the syringe, and driving means (500) to move the push device (300) toward the syringe (400) at the desired speed.

Figure 1:
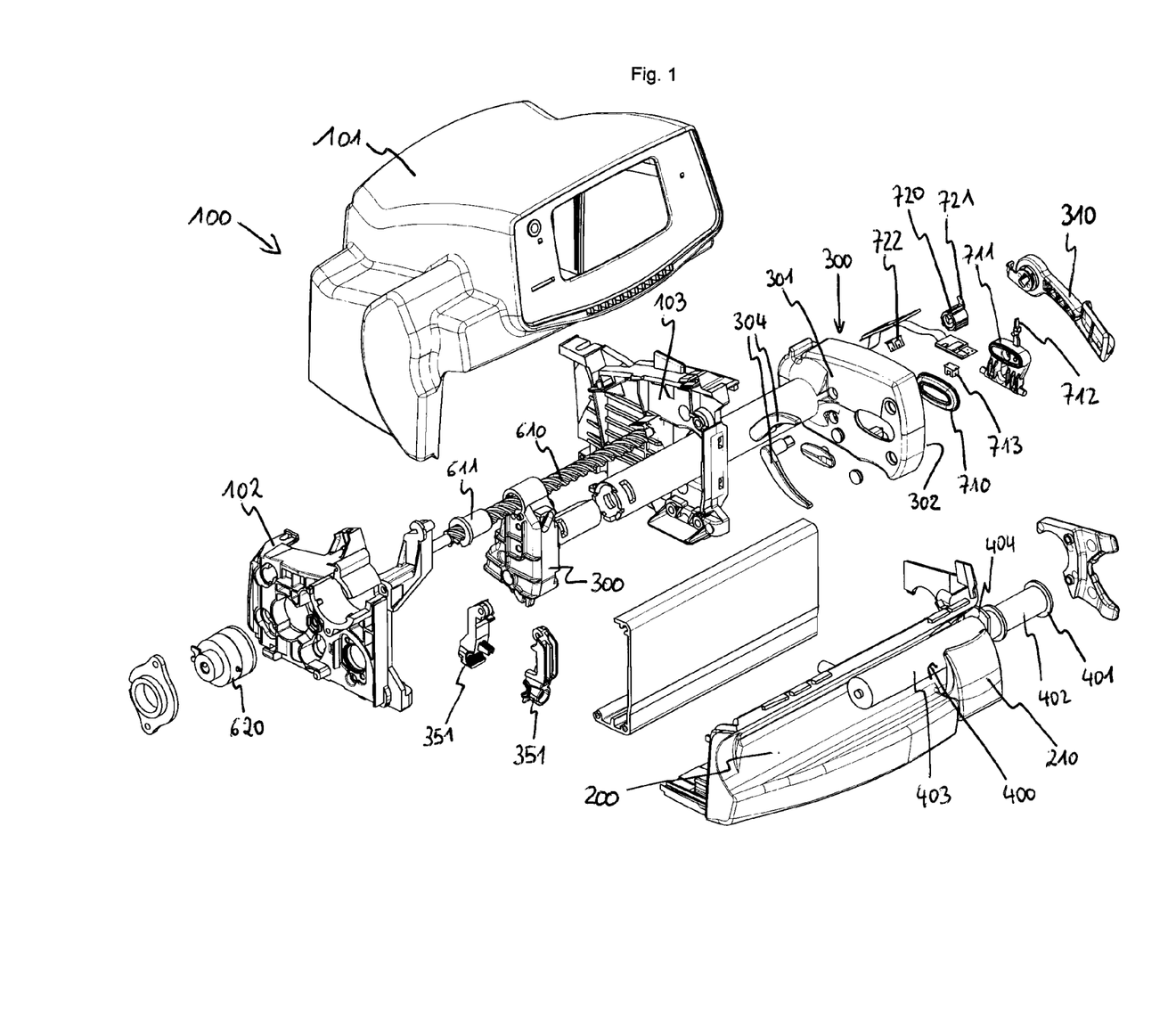
FIG. 1: an exploded view of the main elements of the pump of the syringe driver-type of the invention, without the means for driving the push device.
Figure 2:
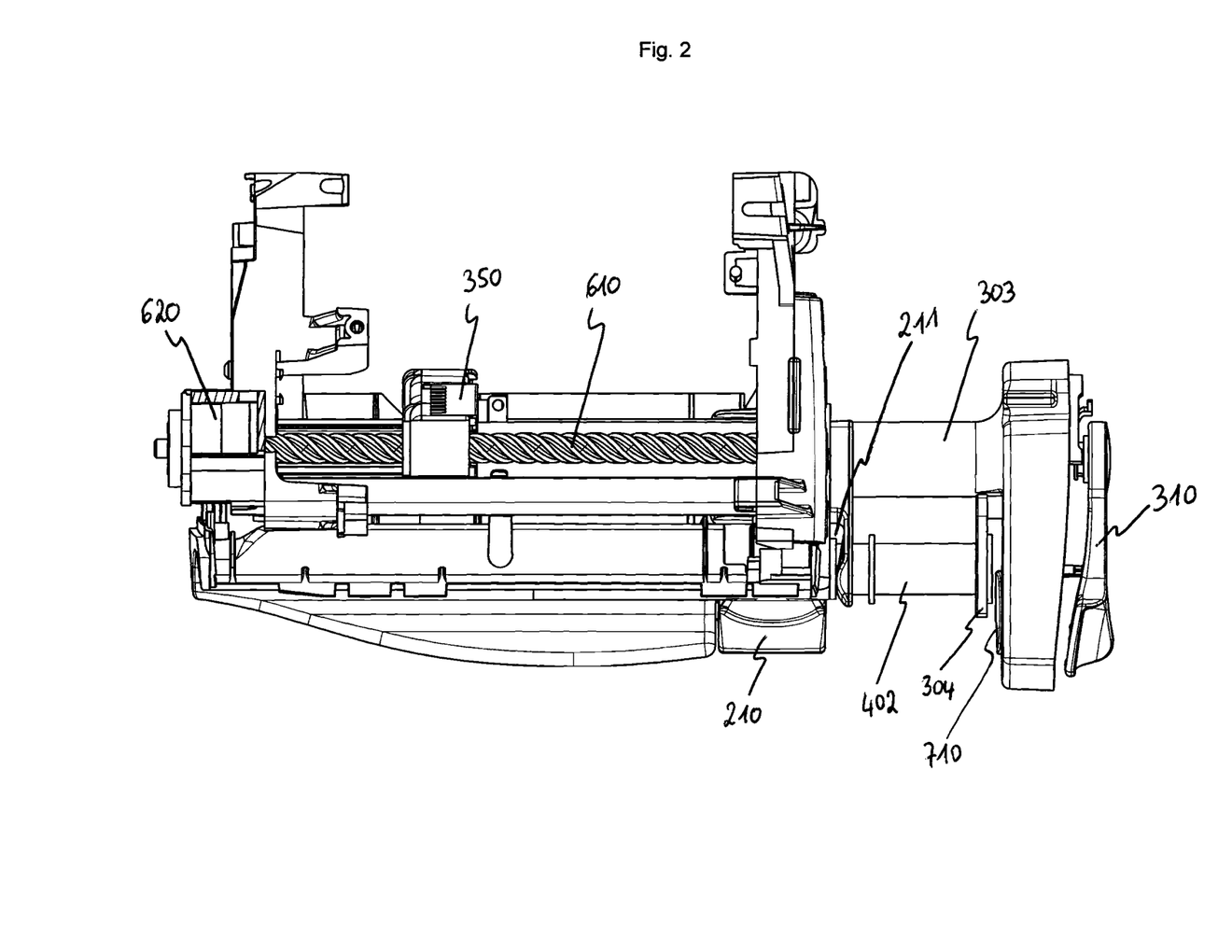
FIG. 2: a top view of the pump of FIG. 1 without the lid.

The casing (100) is constituted in particular by a lid (101), two lateral flanges (102, 103), one (102) of which, the left one on FIG. 1, carries the motor and is called motor flange.

In a known way, the syringe cradle (200) is equipped with means to block the syringe (400) in a radial direction as well as in an axial direction. These means are constituted, on the one hand, by a blocking lever (210), and on the other hand, by a slot (211) in which the fin (404) of the cylinder (403) of the syringe can penetrate.

Figure 6:
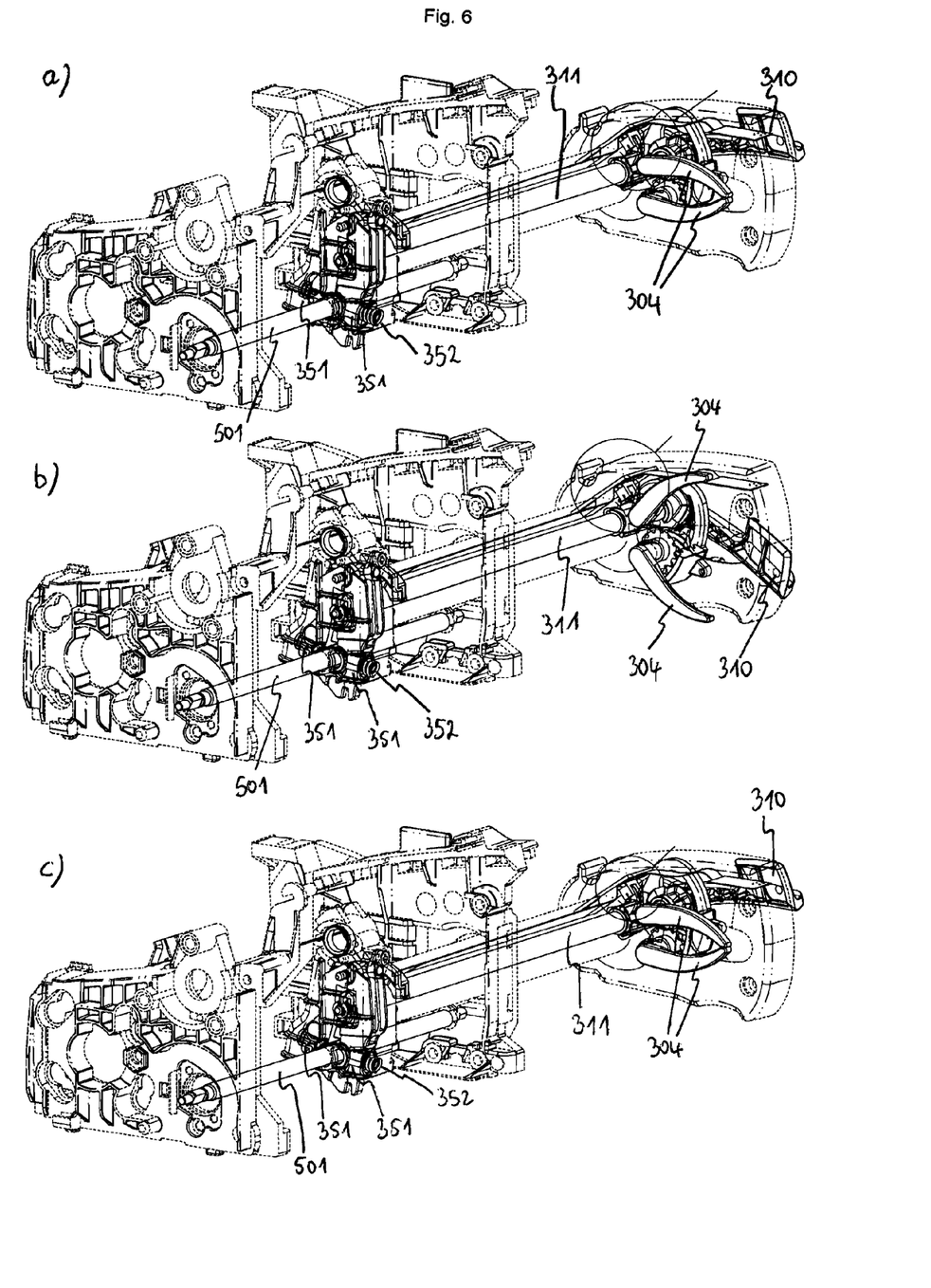
FIG. 6: views of the clutch means a) in engaged position, b) in disengaged position and c) in partial engagement position.

Similarly, the push device (300) is equipped with means for blocking the syringe head (401) against its front face (301), oriented toward the syringe. These blocking means are constituted by two pivotable arms (304) which can be moved away from each other to let the syringe head (401) pass, or brought close to each other to block the syringe head on the front face 301 of the push device (see FIGS. 6 and 9).

Figure 3:
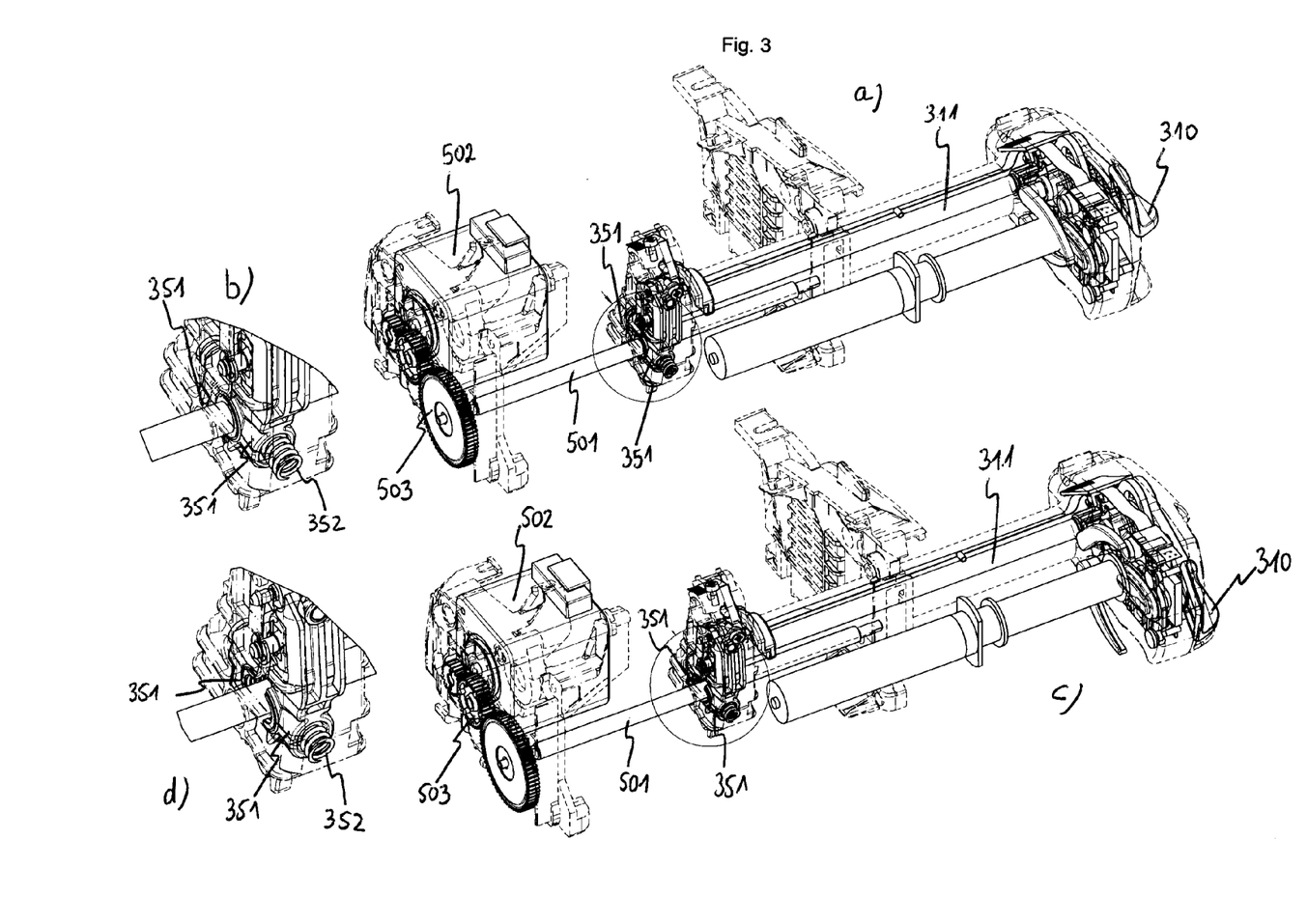
FIG. 3: a partial view of the pump of FIG. 1 showing the driving means a) and b) in engaged position, c) and d) in disengaged position, a) and c) showing general views, b) and d) detailed views of the half-nuts.
Figure 4:
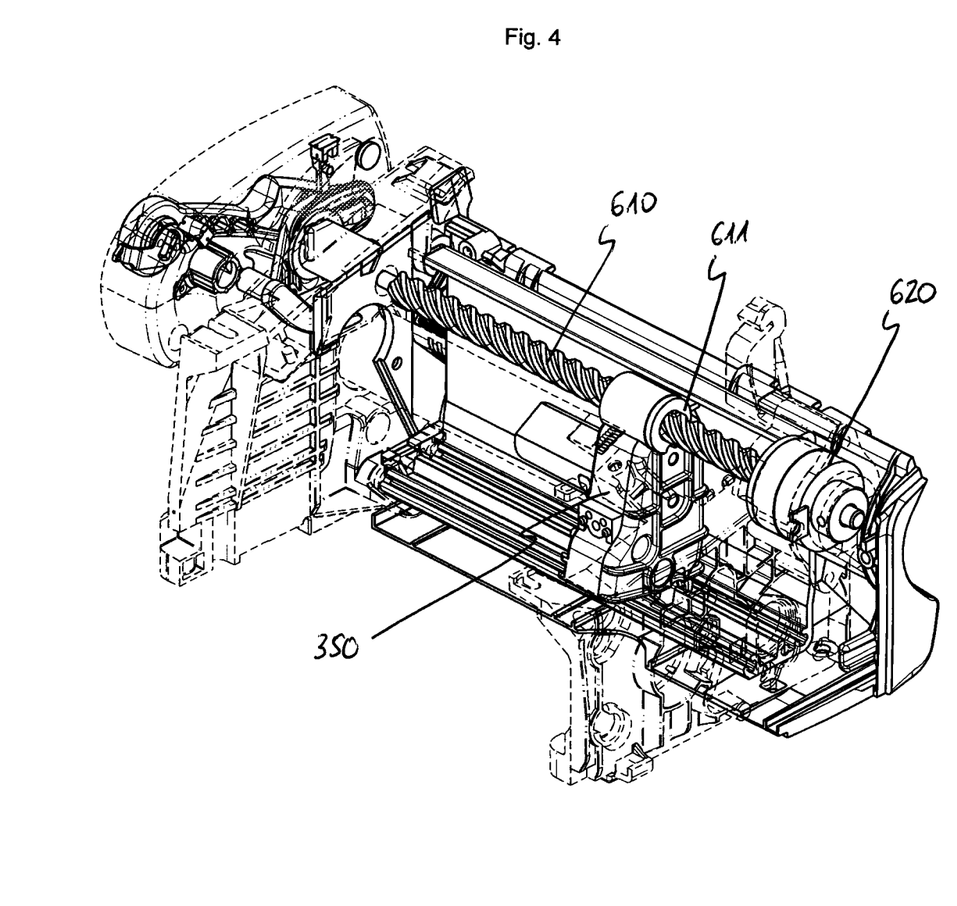
FIG. 4: a partial view of the pump of FIG. 1 showing the control means.

The driving means (500), visible in particular on FIG. 3, are constituted by a threaded driving rod (501) coupled to a motor (502) via a reducer (503). These three organs are preferably placed inside the casing.

Figure 8:
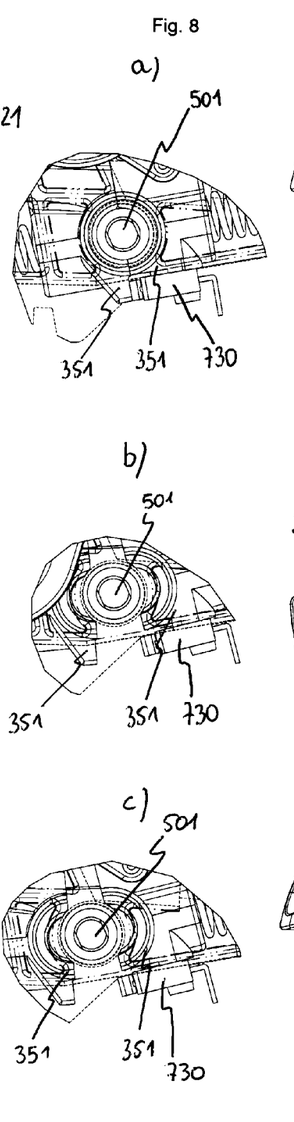
FIG. 8: detailed views of the half-nuts in the positions of FIG. 6.

The push device (300) is fixed at the end of a linking bar (303) in the form of a tube whose other end is fixed to a cart (350) mobile inside the casing. This cart (350) is coupled to the threaded driving rod (501) via a nut. This nut is itself constituted by two mobile half-nuts (351) capable of being moved from a so-called engaged position to a so-called disengaged position, and vice versa. In the engaged position, clearly visible on FIG. 8*a*, the half-nuts (351) surround the threaded driving rod (501) so as to cooperate with it to translate the cart (350) along the threaded driving rod (501) when the motor is started. In the disengaged position (cf. FIG. 8*b*), on the contrary, the two half-nuts (351) are moved away from each other so that they no longer cooperate with the threaded driving rod (501). These two positions are also represented in particular on FIG. 3, wherein FIG. 3b shows the engaged position whereas FIG. 3d shows the disengaged position. In the disengaged position, it is thus possible to move the cart (35) manually along the threaded driving rod (501) without starting the motor (502).

The push device is equipped with disengaging means in order to move it manually. These disengaging means are constituted by a lever (310) fixed at the end of a push rod (311) which is placed inside a linking bar (303). This lever is placed on the rear face (302) of the push device, which face is opposed to the face intended to push the syringe head. At the other extremity of the push rod (311) is located a cam (not shown) which cooperate with the half-nuts (351) to bring them apart. Springs (352) tend to bring them together to position them in the engaged position, whereas the cam located at the end of the push cam (311) moves them away from each other when the lever (310) is actuated.

Figure 5:
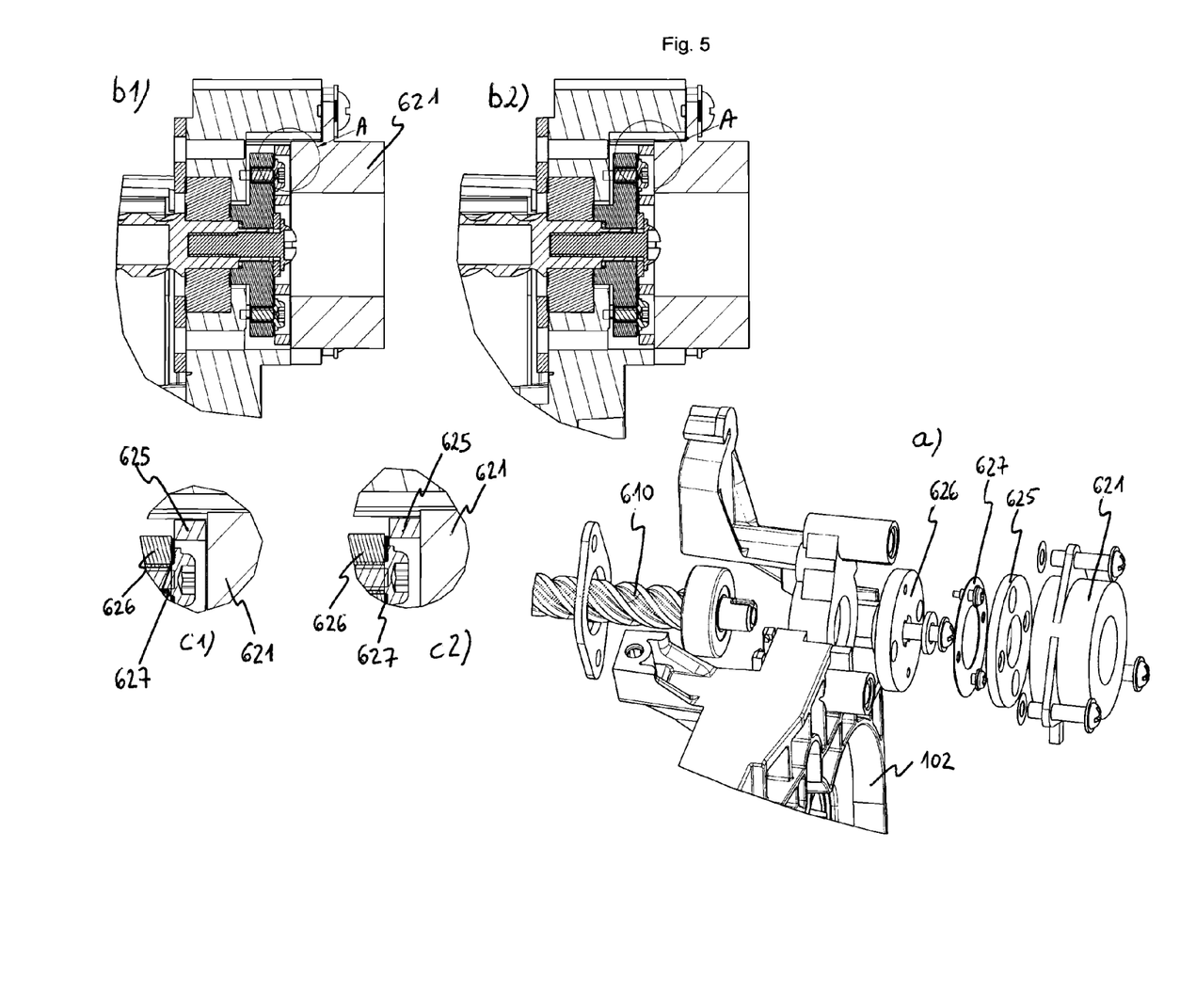
FIG. 5: a detailed exploded view of the electromagnetic brake, b1) a detailed cross-sectional view of the electromagnetic brake in deactivated position and b2) in activated position, c1) a detailed view A in deactivated position and c2) in activated position.

Beyond these organs common to pumps of the state of the art, the syringe driver of the invention comprises control means (600) which make it possible to block instantaneously the approach movement of the push device (300) in the direction of the syringe head (401). These control means are shown in detail on FIG. 5. They are constituted, on the one hand, by a threaded control rod (610) on which is mounted a nut (611) which is linked to the cart (350) via a connection by fitting, and on the other hand, by an electromagnetic brake (620). This electromagnetic brake is constituted by a stator (621) fixed to the motor flange (102) and a rotor constituted by a pad (625) fixed with a certain axial play to the threaded control rod (610) via the hub (626). An elastic element (627) is interposed between the pad (625) and the hub (626). As long as the electromagnetic brake (620) is not actuated, the pad (625) is kept away from the stator (621) by the elastic element (627) and the threaded control rod (610) can freely rotate. The cart (350) can thus be moved in translation along this threaded control rod (610), either by the action of the driving means (500) or during a manual displacement, which triggers the rotation of the threaded control rod (610). In fact, the profile of the thread of the threaded control rod (600) as well as the nut (601) is reversible. If, on the contrary, the electromagnetic brake is activated, the windings contained in the stator (621) are powered and the pad (625) comes to press against the static portion (621) of the electromagnetic brake. The rotation of the threaded control rod (610) is blocked. Since the control nut (611) is itself blocked in rotation by fitting in the cart 350), the whole cart (350), and, with it, the push device (300), are blocked in translation.

In order to function, the control device uses several sensors. A first sensor makes it possible to detect if the push device (300) is in contact with the syringe head (401). This contact sensor is constituted by a detection finger (710) which makes it possible to tilt a rocker (711). This rocker is equipped in its upper portion with a vane (712) that cooperates with an optical detector (713). In the protruding position of the detection finger (710), i.e., without contact with the syringe head, the vane penetrates into the optical detector (713). If, on the contrary, the detection finger (710) is withdrawn, i.e., if the push device (300) is in contact with the syringe head, then the vane (712) comes out of the optical detector (713), and the latter changes states. This change is used to actuate the electromagnetic brake (620). In a variant embodiment, the vane is located outside of the optical detector when the detection finger is in the protruding position and penetrates into the detector when the detection finger is withdrawn.

Figure 7:
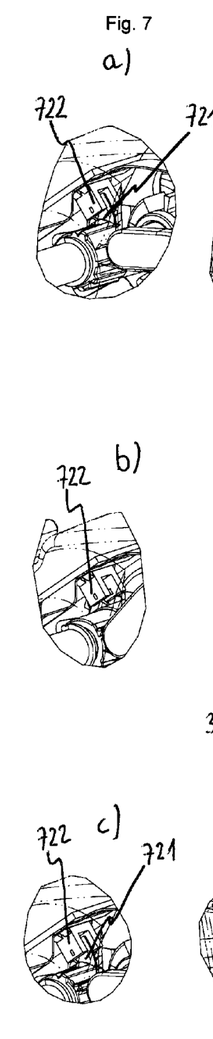
FIG. 7: views of the clutch lever in the positions of FIG. 6.
Figure 9:
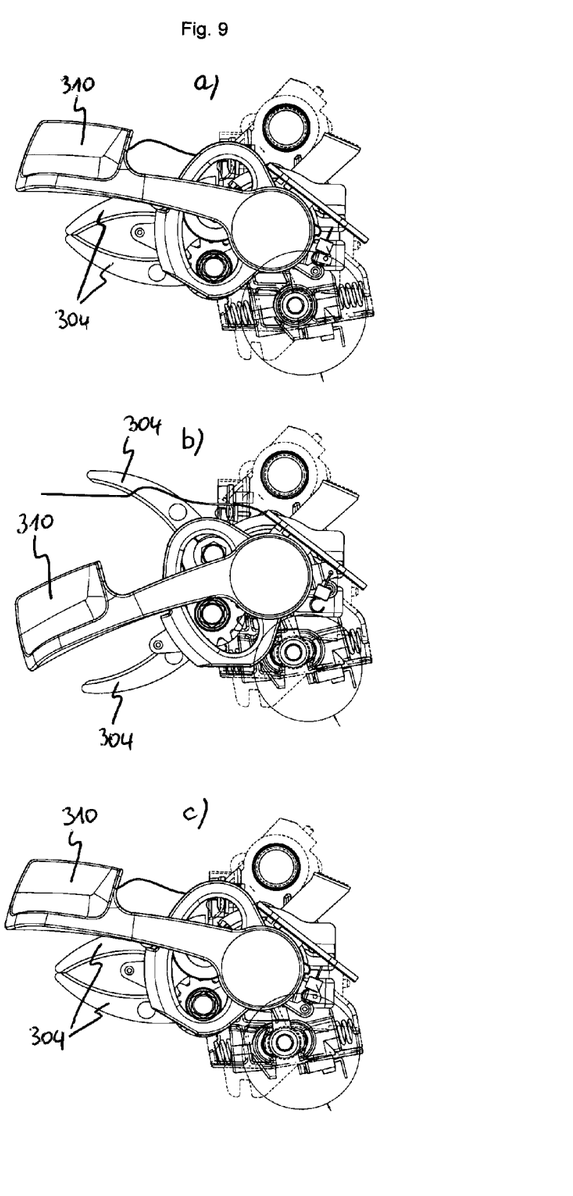
FIG. 9: detailed views of the opto sensor located in the area of the lever in the positions of FIG. 6.
Figure 10:
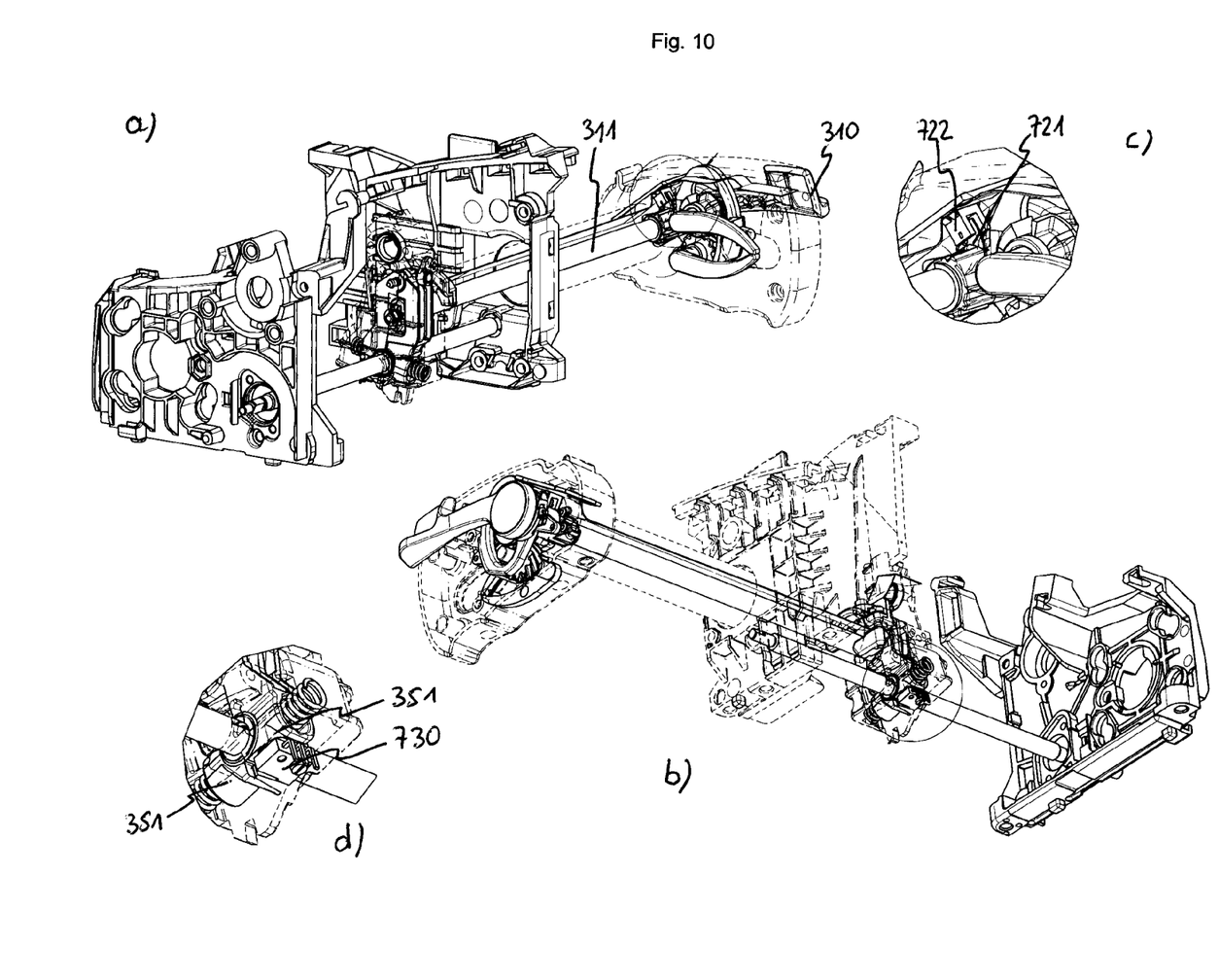
FIG. 10: views of the clutch means in the engaged position, a) general top perspective view and b) bottom perspective view, c) detailed view of the opto sensor of the lever and d) detailed view of the switch of the half-nuts.
Figure 11:
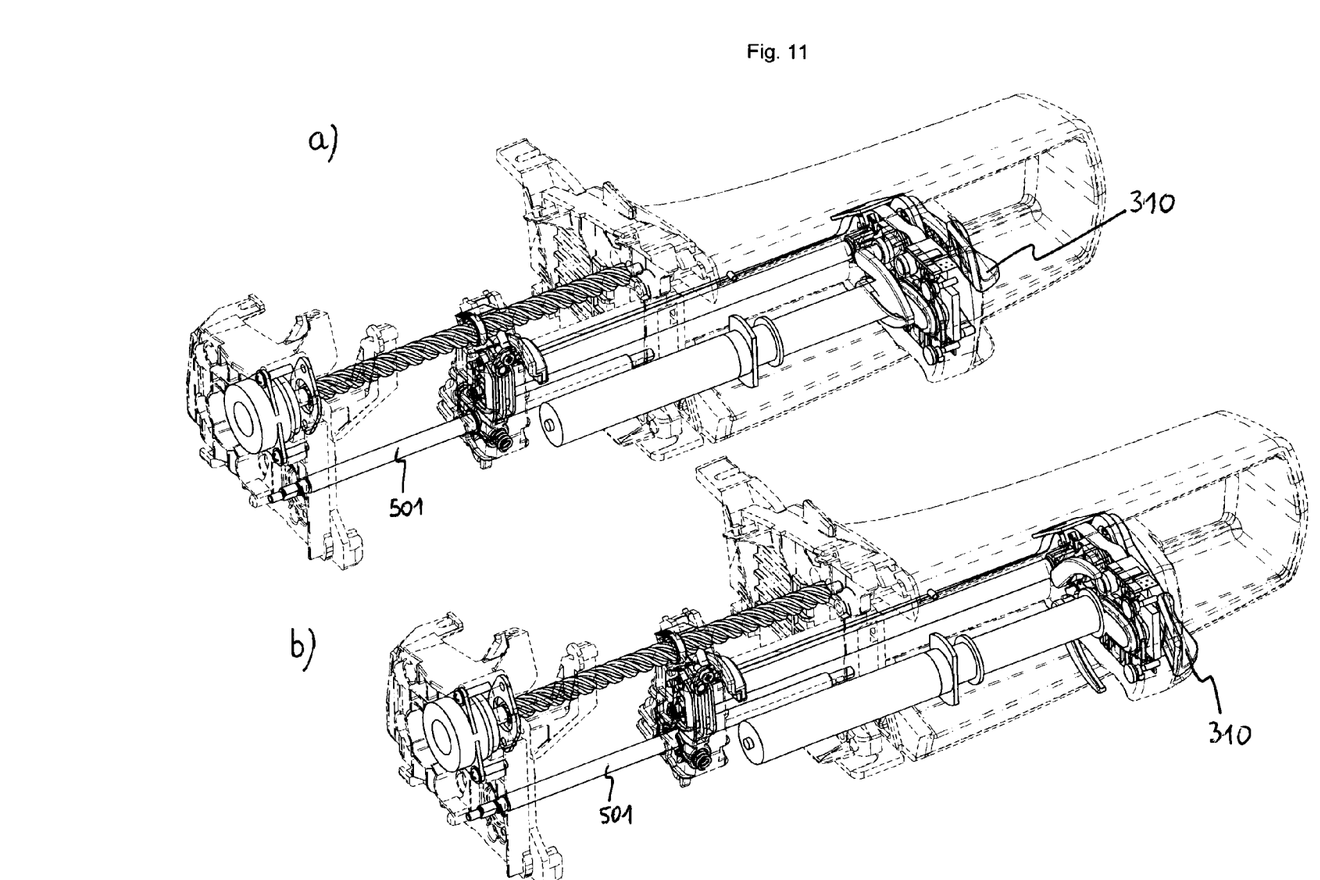
FIG. 11: partial general views of the pump showing the driving means, the control means and the clutch means a) in engaged position and b) in disengaged position.

In addition to this contact sensor, the control device also comprises an engagement sensor. It is constituted by a ring (720) integral with the push rod (311) and it carries a vane (721) which cooperates with an optical sensor (722). As long as the lever (310) is in rest position (engaged position), the vane (721) is located in the optical sensor (722), thus providing an engagement signal. If, on the contrary, the lever (310) is pushed down (disengaged position), the vane (721) comes out of the optical sensor (722), which thus provides a disengagement signal. The position of the vane (721) in the optical sensor (722) as a function of the position of the lever (310) is clearly visible on FIGS. 7a/7c and 9a/9c for the engaged position and on FIGS. 7b and 9b for the disengaged position.

The anti-bolus control procedure operates in the following manner. The push device (300) is in the moved-away position, at a distance behind the syringe head (401), which is placed in a conventional manner in the syringe cradle (200). The detection finger (710) protrudes slightly from the front face (301) of the push device (300) and the optical contact sensor (713) provides a signal of absence of contact. Since the lever is in rest position, the optical engagement sensor (722) provides an engagement signal. The electromagnetic brake is not activated.

The lever (310) is then actuated by lowering it. The optical engagement sensor (722) provides a disengagement sensor. The push rod (311) rotates, driving with it the cam which moves the half-nuts (351) away from each other. It is now possible to move the push device (300) toward the syringe. The movement of the push device (300) causes the movement of the cart (350) via the linking bar (303). As for the movement of the cart (350), it causes the rotation of the threaded control rod (610) via the nut (611).

As soon as the push device (300) comes in contact with the syringe head (401), the detection finger (710) is pushed in, triggering the tilting of the rocker (711) and the withdrawal of the vane (712) out of the optical contact detector (713). The latter emits a contact signal which is used to actuate the electromagnetic brake (620). The windings contained in the stator (621) are powered and the pad (625) comes to press itself against the stator, thus blocking the rotation of the threaded control rod (610). In the previously mentioned variant, pushing the detection finger causes the vane to penetrate into the optical detector.

Parallel to the engagement sensor, there is also a sensor (730) of the position of the half-nuts (351). Pushing the lever (310) down causes the push rod (311) to rotate and the half-nuts (351) to move away from each other via the spreading cam, whereas return of the lever (310) to rest position causes the push rod (311) to rotate in the reversed direction and the cam to return to rest position. Under the action of the springs (352), the half-nuts (351) should return in closed engagement position. However, following the manual displacement of the cart (350), it is possible that the threads of the half-nuts (351) do not face the thread of the threaded driving rod (501). In this case, the half-nuts (351) cannot return to their engagement position even though the lever is in rest position. Thus, a switch-type sensor (730) located on the half-nuts (351) is provided. If the half-nuts are moved away from each other, as on FIGS. 8b and 8c, this position sensor provides a spread position signal (or disengagement signal). On the contrary, if they are in closed position, as on FIG. 8a, it provides a near position signal (or engagement signal).

Thus, the clutch control functions according to the following table:

TABLE 1 clutch control

| Position | Engagement sensor (722) signal | Position sensor (730) signal |
|---|---|---|
| Engaged position (FIGS. 6a, 7a, 8a, 9a); Lever in rest position; Half-nuts in closed position | Engaged | Closed |
| Disengaged position (FIGS. 6b, 7b, 8b, 9b); Lever pushed down; Half-nuts in spread position | Disengaged | Spread |
| Intermediary position (FIGS. 6c, 7c, 8c, 9c); Lever in rest position; Half-nuts in spread position | Engaged | Spread |

In the case of the intermediary position, since this position runs the risk of being reached during the passage from the disengaged position to the engaged position following a manual displacement of the push device, a specific sequence must be performed so that the half-nuts (351) come back into their housing in the area of the threaded driving rod (501). This procedure consists of setting the threaded driving rod (501) in rotation, preferably by controlling the force generated by the push device on the syringe via a force sensor integrated into the push device (not shown), until the half-nuts (351) have reached the engaged position. In this way, it is ensured that the push device, when it comes in contact with the syringe head, acts on the syringe with a force that is neither too high nor too low. If the push device pressed on the syringe head with a force that is too high, it would trigger an involuntary bolus. If, on the contrary, it pressed on the syringe head with a force that is too low, there would be a delay in the administration of the drug at the beginning of the perfusion, because the push device must first be displaced for a certain amount of time toward the syringe before it starts moving the syringe head.

Thanks to this control device, it is thus possible, without intervening directly on the syringe, to block the movement of the push device as soon as it comes in contact with the syringe head. However, it can be desirable to apply a voluntary bolus. To this effect, a manual displacement of the push device must be permitted even though it is in contact with the syringe head. To this effect, the method provides that the electromagnetic brake (620) is not activated if the lever is pushed down when the contact sensor (713) already transmits a contact signal. Thus, it is possible to administrate a voluntary bolus, either during the perfusion, or directly after the push device has been contacted with the syringe head. In the latter case, in order to be able to move the push device after it has been contacted with the syringe head, one must, first of all, release the lever to give an engagement signal, and then push the lever down again and move the push device with the syringe head toward the syringe.

Table 2 summarizes the control method and indicates the succession of the various steps as a function of the initial situation.

TABLE 2

Successive steps in the anti-bolus control method

| Initial situation | Sensor signals | Consequences |
|---|---|---|
| Push device moved away Lever in rest position | 713: no contact 722: engaged 730: engaged | It is not possible to move the push device manually |
| Lever pushed down | 713: no contact 722: disengaged 730: disengaged | It is possible to move the push device manually |
| Movement of the push device toward the syringe | 713: no contact 722: disengaged 730: disengaged | |
| Push device comes in contact with the syringe head | 713: contact 722: disengaged 730: disengaged | Activation of the electromagnetic brake: blocking of the push device translation |
| Release of the lever | 713: contact 722: engaged 730: engaged/ disengaged*) | Deactivation of the electromagnetic brake: unblocking of the translation of the push device. It is not possible to move the push device manually. |
| Actuation of the motor | 713: contact 722: engaged 730: engaged | |
| Lever pushed down to administrate a voluntary bolus | 713: contact 722: disengaged 730: disengaged | No activation of the electromagnetic brake, because contact push device/syringe at the beginning of the maneuver. |
| Manual displacement of the push device | 713: contact 722: disengaged 730: disengaged | Administration of a voluntary bolus. |
| Release of the lever | 713: contact 722: disengaged 730: engaged/ disengaged*) | |

*)In the case of non-alignment of the threads of the half-nuts with the thread of the threaded driving rod, the alignment procedure must be performed.

The control method can be translated in the following manner:

Step a): Disengage the push device (300) from the driving means (500) by pushing on the lever (310). This causes the half-nuts (351) to move away from each other. The disengagement sensor (722) is in disengaged position, the position sensor (730) of the half-nuts is in spread position.

Step b): The device detects the presence or absence of contact between the push device (300) and the syringe head (401) by exploiting the contact signal of the contact sensor (713). If the sensor contact is in non-contact position, the procedure continues at step c). If the contact sensor is in contact position, the procedure continues at step g').

Step c): If the contact sensor (713) is in non-contact position, the push device (300) is moved in translation toward the syringe until it comes in contact with the syringe head, which causes the contact sensor (713) to change to contact position. This change from the non-contact position to the contact position causes the activation of the electromagnetic brake (620), and thus, blocking of the translation of the push device. During this entire step, the piston (402) of the syringe is free, and thus, it could be moved toward the syringe or the push device by other means that the driving means, for example, with a finger.

Step d): Once the push device (300) is in contact with the syringe head (401) and the electromagnetic brake (620) is actuated, it is again possible to engage the push device on the driving means (500) by releasing the lever (310). The half-nuts (351) are moved toward each other until they cooperate again with the threaded driving rod (501). The contact sensor (713) remains in contact position, the engagement sensor (722) returns to the engaged position and the position sensor (730) returns to the near position, wherein, as the case may be, the alignment procedure of steps d') and d") is performed.

Step e): The push device (300) being engaged on the driving means (500), it is not possible to move the push device otherwise than with the motor (502). It is thus possible to deactivate the electromagnetic brake (620) and thus to unblock the translation movement of the push device (300). According to the needs, the procedure continues at step i) by starting the motor and the perfusion, or it continues at step f) by administering a voluntary bolus.

Step f): If, now, the push device (300) is in contact with the syringe head (401), in other words, if the contact sensor (713) is in contact position, and the operator wants to administrate a voluntary bolus, the operator disengages once again the push device from the driving means by pushing on the lever (310). Once again, the half-nuts (351) are moved away from the threaded driving rod (501).

The engagement sensor (722) changes again to the disengaged position and the position sensor (730) of the half-nuts (351) changes to the spread position. This time, the change of the engagement sensor (722) from the engaged position to the disengaged position while the contact sensor (713) is in contact position does not cause the activation of the electromagnetic brake, because this latter sensor (713) is already in contact position.

Step g): The push device (300), and, with it, the syringe head (401), are moved in translation toward the syringe (400) by the desired distance to administrate the desired amount of product. The lever (310) remains in pushed position during this entire step.

Step h): Once the desired volume has been administered, the displacement of the push device (300) is stopped and it is engaged on the driving means (500). To this effect, the lever (310) is released and the half-nuts (351) return to the position cooperating with the threaded driving rod (501). The contact sensor (713) is in contact position, the engagement sensor (722) is in engaged position and the position sensor (730) is in near position, as the case may be, after having performed steps h") and h"').

Step g'): If, at step b), the contact sensor (713) is in contact position, in other words, if the push device (300) is already in contact with the syringe head, it is possible to administer directly a voluntary bolus. After step b), the position sensor (713) is in contact position, the engagement sensor (722) is in disengaged position, and the position sensor (730) is in spread position. Thus, it is now possible to move the push device in translation, and with it, the syringe head, toward the syringe by the desired distance to administer the desired amount of product. The lever (310) remains in pushed position during this entire step.

Step h'): Once the desired volume has been administered, the displacement of the push device is stopped and it is engaged on the driving means. To this effect, the lever (310) is released and the half-nuts (351) return in position cooperating with the threaded driving rod (501). The contact sensor (713) is in contact position, the engagement sensor (722) is in engagement position and the position sensor (730) is in near position, as the case may be, after having performed steps h") and h"').

Step i): The driving means (500) are started to perform the perfusion. The contact sensor (713) is in contact position, the engagement sensor (722) is in engagement position and the position sensor (730) in near position. Of course, it is possible to administrate a voluntary bolus during the perfusion, by continuing the procedure of step g').

Step d') and

Step h"): After each manual displacement of the push device, the relative position of the half-nuts (351) is detected using the position sensor (730). If the threads of the half-nuts (351) are engaged in the thread of the threaded driving rod (501), there is no problem and the procedure can follow its course with step e) or step i).

Step d") and

Step h"'): If, on the contrary, the threads of the half-nuts (351) are not aligned with the thread of the threaded driving rod (501), they cannot come close enough to each other to cooperate with it. Even though the engagement sensor (722) is in engagement position, the position sensor (730) remains in spread position (cf. FIGS. 7*c*) and 8*c*)). An alignment procedure must then be performed, consisting, for example, in setting in rotation the threaded driving rod (501), while preferably controlling the force generated by the push device on the syringe via the force sensor integrated into the push device, until the threads of the half-nuts are aligned with the thread of the threaded driving rod. In this position, the half-nuts, pushed by the springs, fall back into their position near each other. The position sensor (730) then transmits a near position signal and the rotation of the threaded driving rod (501) is stopped. The normal procedure can thus continue at step e) or step i).

The control method always begins by disengaging the push device (step a). In fact, whatever the procedure to be performed (preparation of the pump by contacting the push device with the syringe head, or bolus administration), one must first disengage the push device from the driving means to enable a manual displacement of the push device. As soon as the push device is in disengaged position, the method determines the position of the push device with respect to the syringe head (step b).

If the method does not detect a contact with the syringe head, it is possible to push the push device until it comes in contact with the syringe head (step c). Once this position has been reached, the method blocks the movement of the push device. The user must again engage the push device on the driving means (step d). The blocking device is then deactivated (step e). Depending on needs, it is now possible to administer a voluntary bolus (steps f, g, h) or to start the pump (step i). To administrate a voluntary bolus, one must again actuate the lever and disengage the push device from the driving means (step f). It is also possible to move the push device away from the syringe, i.e., to go in reverse.

If, on the contrary, the method detects that the push device is in contact with the syringe head (step b), it is possible to apply a voluntary bolus (steps g', h'). In other words, during pumping, it is enough to actuate the lever once to be able to administer a voluntary bolus.

Thanks to the method and device of the invention, it is possible, not only to avoid an involuntary bolus when the push device is moved toward the syringe head, and this, without intervening on the syringe itself, but also to administer a voluntary bolus at any time, either directly after the push device has come in contact with the syringe head, or during the perfusion. Since no radial force is applied on the piston of the syringe, there is no risk that it would move out of axis and thus, become stuck in the cylinder.

Reference List

100 Casing
　101
　102 lateral flange (motor flange)
　103 lateral flange
200 Syringe cradle
　210 Blocking lever
　211 Blocking slot
300 Push device
　301 Front face of the push device
　302 Rear face of the push device
　303 Linking bar
　304 Pivoting arms
　310 Disengagement lever
　311 Push rod
　350 Cart
　351 Half-nuts
　352 Springs
400 Syringe
　401 Syringe head
　402 Syringe piston
　403 Syringe cylinder
　404 Fins of the syringe cylinder
500 Driving means
　501 Threaded driving rod
　502 Motor
　503 Reducer
600 Control means
　610 Threaded control rod
　611 Nut
　620 Electromagnetic brake
　621 Stator
　625 Pad
　626 Hub
　627 Elastic element
　710 Detection finger
　711 Rocker
　712 Vane of the rocker
　713 Optical contact sensor
　720 Ring
　721 Vane of the ring
　722 Optical engagement sensor
　730 Position sensor of the half-nuts (switch)

The invention claimed is:

1. Method of controlling the movement of a push device of a pump of the syringe driver-type, the pump comprising a casing, a syringe cradle in which a syringe is placed, a push device mobile relative to the casing and capable of being driven in translation parallel to the longitudinal axis of the syringe, and a clutch having an engaged configuration engaging the push device to be driven in translation and a disengaged configuration disengaging the push device from being driven in translation, said method comprising:
   a) setting the clutch in the disengaged configuration disengaging the push device;
   b) detecting the presence or absence of contact between the push device and a piston head of the syringe;
   c) detecting the absence of contact between the push device and the piston head of the syringe, and while the push device is disengaged, moving the push device in translation toward the syringe until there is contact between the push device and the piston head of the syringe, detecting the contact of the push device with the piston head of the syringe, and immediately blocking the translation movement of the push device, wherein said blocking had been inactivated up to then.

2. Method according to claim 1, comprising the following additional steps performed after step c):
   d) setting the clutch in the engaged configuration engaging the push device;
   e) unblocking the translation movement of the push device.

3. Method according to claim 2, comprising the following additional steps performed after step e):
   f) setting the clutch in the disengaged configuration disengaging the push device;
   g) moving in translation, by the desired amplitude, the push device in contact with the piston head in the direction of the syringe;
   h) stopping the movement of the push device and setting the clutch in the engaged configuration engaging the push device.

4. Method according to claim 1, comprising the following additional steps performed after step b):
   b') detecting the presence of a contact between the push device and the piston head, and moving in translation, by the desired amplitude, the push device in contact with the piston head in the direction of the syringe;
   b") stopping the movement of the push device and setting the clutch in the engaged configuration engaging the push device.

5. Method according to claim 2, comprising the following additional step performed after step e):
   e') driving the push device in translation.

6. Method according to claim 2, said method being applied to a pump whose push device is driven by a threaded driving rod by two half-nuts capable of being moved between an engaged position in which the two half-nuts are brought close to each other and surrounding the threaded driving rod so that they can move on the threaded driving rod only when the threaded driving rod is set in rotation, and a disengaged position in which the two half-nuts are brought away from each other and from the threaded driving rod so that they no longer cooperate with the threaded driving rod, said method comprising the following intermediate steps performed after the engagement of step d):
   d') detecting the relative position of the half-nuts;
   d") if the two half-nuts have not reached the engaged position, setting the threaded driving rod in rotation, until the two half-nuts have reached the engaged position.

7. Pump of the syringe driver-type comprising
   a casing,
   a syringe cradle intended to receive a syringe,
   a push device mobile relative to the casing and capable of being driven in translation parallel to the longitudinal axis of the syringe,
   a clutch having an engaged configuration engaging the push device to be driven in translation and a disengaged configuration disengaging the push device from being driven in translation, and
   means for blocking the movement of the push device toward the syringe when the push device contacts a piston head of the syringe during a movement from a position without contact with the piston head of the syringe toward a position in contact with the piston head of the syringe,
   wherein the means for blocking the push device comprise (i) a threaded control rod, (ii) a threaded nut engaged on the threaded control rod and integral with the push device, and (iii) a brake acting on the threaded control rod.

8. Pump according to claim 7, wherein the brake is constituted by an electromagnetic brake comprising a rotor integral with the threaded control rod and a stator integral with the casing.

9. Pump according to claim 7, wherein the push device is equipped with a contact sensor to detect the presence or absence of contact between the push device and the piston head.

10. Pump according to claim 7, wherein the the push device is driven by a threaded driving rod driven in rotation by a motor.

11. Pump according to claim 10, wherein the clutch comprises a clutch lever located outside the casing, a push rod integral with the lever and two half-nuts capable of being moved from an engaged position in which they surround the threaded driving rod so as to be capable of cooperating with it and a disengaged position in which they are moved away from the threaded driving rod so that they do not cooperate with it.

12. Pump according to claim 7, wherein at least one engagement sensor is provided to determine if the push device is engaged or disengaged on the clutch.

13. Pump according to claim 12, wherein the engagement sensor or sensors are placed on at least one of (i) the push device and (ii) the clutch.

14. Method according to claim 6, wherein, in step d"), if the two half-nuts have not reached the engaged position, the threaded driving rod is set in rotation by controlling the effort generated by the push device on the syringe via a force sensor integrated with the push device.

15. Method according to claim 3, comprising the following additional step performed after step h):
i) driving the push device in translation.

16. Method according to claim 4, comprising the following additional step performed after step b"):
b''') driving the push device in translation.

17. Method according to claim 3, said method being applied to a pump whose push device is driven by a threaded driving rod by two half-nuts capable of being moved between an engaged position in which the two half-nuts are brought close to each other and surrounding the threaded driving rod so that they can move on the threaded driving rod only when the threaded driving rod is set in rotation, and a disengaged position in which the two half-nuts are brought away from each other and from the threaded driving rod so that they no longer cooperate with the threaded driving rod, said method comprising the following intermediate steps performed after the engagement of step h):
h') detecting the relative position of the half-nuts;
h") if the two half-nuts have not reached the engaged position, setting the threaded driving rod in rotation, until the two half-nuts have reached the engaged position.

18. Method according to claim 4, said method being applied to a pump whose push device is driven by a threaded driving rod by two half-nuts capable of being moved between an engaged position in which the two half-nuts are brought close to each other and surrounding the threaded driving rod so that they can move on the threaded driving rod only when the threaded driving rod is set in rotation, and a disengaged position in which the two half-nuts are brought away from each other and from the threaded driving rod so that they no longer cooperate with the threaded driving rod, said method comprising the following intermediate steps performed after the engagement of step b"):
b''') detecting the relative position of the half-nuts;
b'''') if the two half-nuts have not reached the engaged position, setting the threaded driving rod in rotation, until the two half-nuts have reached the engaged position.

19. Pump according to claim 8, wherein the push device is equipped with a contact sensor to detect the presence or absence of contact between the push device and the piston head.

20. Pump according to claim 8, wherein the the push device is driven by a threaded driving rod driven in rotation by a motor.

21. Pump according to claim 11, wherein the push device comprises a force sensor that detects if the two half-nuts have not reached the engaged position when engaging the push device, so that the threaded driving rod is set in rotation by controlling the effort generated by the push device on the syringe via a force sensor integrated with the push device.

22. Method according to claim 1, wherein the push device is being driven in translation by a motor.

23. Method according to claim 1, wherein the push device is being driven in translation by driving means.

24. Method according to claim 23, wherein the translation movement of the push device is blocked by actuating means for blocking the translation movement of the push device.

25. Method of controlling the movement of a push device of a pump of the syringe driver-type, the pump comprising a casing, a syringe cradle in which a syringe is placed, a push device mobile relative to the casing and capable of being driven in translation parallel to the longitudinal axis of the syringe, and a clutch having an engaged configuration engaging the push device to be driven in translation and a disengaged configuration disengaging the push device from being driven in translation, the push device being driven by a threaded driving rod by two haft-nuts capable of being moved between an engaged position in which the two half-nuts are brought close to each other and surrounding the threaded driving rod so that they can move on the threaded driving rod when the threaded driving rod is set in rotation, and a disengaged position in which the two half-nuts are brought a from each other and from the threaded driving rod so that they no longer cooperate with the driving rod, said method comprising:
a) setting the clutch in the disengaged configuration disengaging the push device;
b) detecting the presence or absence of contact between the push device and a piston head of the syringe;
b') detecting the presence of a contact between the push device and the piston head, and moving in translation, by the desired amplitude, the push device in contact with the piston head in the direction of the syringe;
b") stopping the movement of the push device and setting the clutch in the engaged configuration engaging the push device,
wherein the method comprises, in order to set the clutch in the engaged configuration in step b"):
b''') detecting the relative position of the half-nuts;
b''''1 if the two half-nuts have not reached the engaged position, setting the threaded driving rod in rotation, until the two half-nuts have reached the engaged position.

26. Method according to claim 25, comprising the following additional step performed after step b"):
b''''')driving the push device in translation.

27. Method according to claim 25, wherein the push device is being driven in translation by a motor.

28. Method according to claim 25, wherein the push device is being driven in translation by driving means.

29. Pump according to claim 7, wherein the push device is being driven in translation by a motor.

30. Pump according to claim 7, wherein the push device is being driven in translation by driving means.

* * * * *